US00RE37971E

(19) United States
(12) Reissued Patent
Baker et al.

(10) Patent Number: US RE37,971 E
(45) Date of Reissued Patent: Jan. 28, 2003

(54) SELECTIVE ACYLATION OF EPSILON-AMINO GROUPS

(75) Inventors: Jeffrey C. Baker, Indianapolis, IN (US); Victor J. Chen, Indianapolis, IN (US); Jose M. Hanquier, Martinville, IN (US); Aidas Kriauciunas, Indianapolis, IN (US); Brian A. Moser, Indianapolis, IN (US); Robert T. Shuman, Greenwood, IN (US)

(73) Assignee: Eli Lilly and Company, Indianapolis, IN (US)

(21) Appl. No.: 09/351,103

(22) Filed: Jul. 8, 1999

Related U.S. Patent Documents

Reissue of:
(64) Patent No.: 5,646,242
Issued: Jul. 8, 1997
Appl. No.: 08/341,231
Filed: Nov. 17, 1994

(51) Int. Cl.[7] ..... A61K 38/28; C07K 16/00
(52) U.S. Cl. ..... 530/303; 514/3
(58) Field of Search ..... 530/303; 514/3

(56) References Cited

U.S. PATENT DOCUMENTS

| | | | | |
|---|---|---|---|---|
| 3,471,464 | A | 10/1969 | Bellet et al. | 260/112.7 |
| 3,528,960 | A | 9/1970 | Haas | 260/112.7 |
| 3,591,574 | A | 7/1971 | Fenichel et al. | 260/112.7 |
| 3,752,798 | A | 8/1973 | Amird et al. | 260/112.7 |
| 3,755,569 | A | 8/1973 | Fenichel et al. | 424/178 |
| 3,823,125 | A | 7/1974 | Grant et al. | 260/112.7 |
| 3,864,325 | A | 2/1975 | Smyth | 260/112.7 |
| 3,868,356 | A | 2/1975 | Smyth | 260/112.7 |
| 3,868,357 | A | 2/1975 | Smyth et al. | 260/112.7 |
| 3,869,437 | A | 3/1975 | Lindsay et al. | 260/112.7 |
| 3,883,496 | A | 5/1975 | Geiger | 260/112.7 |
| 3,883,500 | A | 5/1975 | Geiger et al. | 260/112.7 |
| 3,884,897 | A | 5/1975 | Geiger et al. | 260/112.7 |
| 3,950,517 | A | 4/1976 | Lindsay et al. | 424/178 |
| 4,013,628 | A | 3/1977 | Obermeier et al. | 260/112.7 |
| 4,014,861 | A | 3/1977 | Geiger et al. | 260/112.7 |
| 4,218,539 | A | 8/1980 | Weltman | 435/188 |
| 5,304,473 | A | 4/1994 | Belagaje et al. | 435/69.7 |
| 5,905,140 | A | 5/1999 | Hansen | 530/303 |

FOREIGN PATENT DOCUMENTS

| | | | |
|---|---|---|---|
| EP | 214826 | 8/1986 | C07K/7/10 |
| EP | 383472 | 2/1990 | C07K/7/40 |
| GB | 1260963 | 1/1972 | C07C/103/52 |
| GB | 1415333 | 11/1975 | C07C/103/52 |
| GB | 1492997 | 11/1977 | C07C/103/52 |
| JP | 1-254699 | 10/1989 | C07K/7/40 |
| WO | WO92/01476 | 2/1992 | A61K/47/48 |
| WO | WO95/07931 | 3/1995 | |

OTHER PUBLICATIONS

Geiger, et al., *Biological Activity of Insulin Analogues Substituted at the Amino Group of B1–Phenylalanine,* from Proceedings of the Second International Insulin Symposium, Aachen, Germany, Sep. 4–7, 409–415, (1979).

R. Geiger and R. Obermeier, *Contribution of peptide chemistry to our knowledge of insulin and diabetes,* from Proceedings of the Symposium on Proinsulin, Insulin and C–Peptide, Tokushima, Jul. 12–14, 62–72, (1978).

Rösen, et al, *A1–Modified Insulins: Receptor Binding and Biological Activity,* from Proceedings of the Second International Insulin Symposium, Aachen, Germany, Sep. 4–7, 403–408, (1979).

Hashimoto, et al, *Pharmaceutical Research,* 6:2, 171–176, (1989).

Geiger, *Chemiker Zeitung,* Sonderdruck 100, 111–129, (Translation attached), (1976).

I. MacIntyre and M. Szelke, et al., *Molecular Endocrinology,* Proceedings of Endocrinology '77 held at the Royal College of Physicians, London, England on Jul. 11–15, 27–42, (1977).

W. Scheider, *Journal of Physical Chemistry,* 84:8, 925–928, (1980).

D.G. Lindsay and S. Shall, *BiochemJ.,* 115, 587–595, (1969).*

Muranishi, et al., *Journal of Controlled Release,* 19, 179–188, (1992).*

Hashizume, et al., *J. Pharm. Pharmacol.,* 44 555–559, (1992).*

Lindsay, et al., *Biochem.J.,* 121, 737–745, (1971).*

J.F. Riordan and B.L. Vallee, *Methods of Enzymology,* 25, 494–499, (1972).*

Lapidot, et al., *Journal of Lipid Research,* 8, 142–145, (1967).*

Anderson, et al., *Journal of American Chemical Society,* 86, 1839–1842 (1964).*

Asada, et al., *Pharmaceutical Research,* 11:8, 1115–1120, (1994).*

"The Relative Reactivity of Insulin Amino Groups as n Indicator of Structural Accessibility and its use for Synthetic Approaches for Structure–Function Studies", H.–J. Friesen, (Paper presented in: Insulin, Chemistry, Structure and Function of Insulin and Related Hormones) pp. 125–133, ©1980 Walter de Gruyter & Co., Berlin—New York.

"Acylation and Deacylation of Insulins: Analytical Investigations and Consequences for the Preparation of Derivatives", H.–J. Friesen et al., (Paper presented: Semisynthetic Peptides and Proteins) at the International meeting on Protein Semisynthesis, Sep. 8, 1977, Italy; Academic Press 1978, pp. 160–179 (Edited by: Offord et at., 1978).

* cited by examiner

*Primary Examiner*—Jezia Riley
(74) *Attorney, Agent, or Firm*—Grant E. Reed; Steven P. Caltrider

(57) ABSTRACT

The present invention relates to the acylation of proteins. More particularly, the invention relates to a one-step process for selectively acylating the free ϵ-amino group of insulin, insulin analog, or proinsulin in the presence of a free α-amino group.

63 Claims, No Drawings

SELECTIVE ACYLATION OF EPSILON-AMINO GROUPS

Matter enclosed in heavy brackets [ ] appears in the original patent but forms no part of this reissue specification; matter printed in italics indicates the additions made by reissue.

FIELD OF THE INVENTION

The present invention relates to the acylation of proteins. More particularly, the invention relates to a one-step process for selectively acylating the ϵ-amino group of proinsulin, insulin or an insulin analog in the presence of a free α-amino group.

BACKGROUND OF THE INVENTION

The acylation of amino groups is one of the most common means employed for chemically modifying proteins. General methods of acylation are set forth in Methods of Enzymology, 25:494–499 (1972) and include the use of activated esters, acid halides, or acid anhydrides. The use of activated esters, in particular N-hydroxysuccinimide esters of fatty acids is a particularly advantageous means of acylating a free amino acid with a fatty acid. Lapidot et al., J. of Lipid Res. 8:142–145 (1967). Lapidot et al. describe the preparation of N-hydroxysuccinimide esters and their use in the preparation of N-lauroyl-glycine, N-lauroyl-L-serine, and N-lauroyl-L-glutamic acid.

Early studies of selectively acylating the amino groups of insulin are described in Lindsay et al., in Biochem. J. 121:737–745 (1971). Lindsay et al., describe the reactivity of insulin with N-succinimidyl acetate at low reagent concentration and near neutral pH as producing two mono-substituted products. Phe$^{B1}$-acetyl-insulin and Gly$^{A1}$-acetyl insulin. At pH 8.5, the amount of Phe$^{B1}$-acetyl insulin produced is lowered and Lys$^{B29}$-acetyl-insulin is also produced. Thus, Lindsay et al., conclude at pH 6.9 the order of reactivity is Glycine(A1)≈Phenylalanine(B1)>>Lysine (B29) and at pH 8.5 Glycine(A1)>Phenylalanine=Lysine (B29). Id.

Lindsay et al., U.S. Pat. No. 3,869,437, disclose the acylation of the B$^1$ amino acid with an acyl group containing up to seven carbons and optionally blocking the A$^1$- and/or B$^{29}$-amino group with an acyl group with up to four carbons. N-hydroxysuccinimide esters are described as particularly advantageous acylating agents. In order to produce the maximum yield of insulin acylated at the B$^1$-amino group, the proportion of acylating agent is relatively low (one to not more than two molar equivalents of acylating agent). In addition, the maximum yield of mono-substituted B$^1$ product is produced at a pH at or near about pH 7. At pH 8.5 to 9.0, the yield of the desired B$^1$ acylated product falls off considerably in favor of additional substitution at positions A$^1$ and B$^{29}$.

D. G. Smyth, in U.S. Pat. No. 3,868,356 and Smyth et al., in U.S. Pat. No. 3,868,357 disclose N-acylated, O-substituted insulin derivatives in which at least one of the A$^1$, B$^1$ or B$^{29}$ amino acid amino groups is converted into a blocked amino group. The acylation is carried out with a relatively small excess of acylating agent, e.g., from 2 to 3 moles per amino group at a neutral or mildly alkaline pH, e.g., 7–8. The reaction proceeds in very high yield with the formation of the di-substituted derivative resulting from the reaction of the A$^1$- and B$^1$-amino groups. In the presence of excess acylating agent, e.g., up to 10 molar, the reaction proceeds additionally at the B$^{29}$-amino group to form the tri-substituted derivative.

To selectively acylate insulin, Muranishi and Kiso, in Japanese Patent Application 1-254,699, disclose a five-step synthesis for preparing fatty acid insulin derivatives. Step one, the activated fatty acid ester is prepared; Step two, the amino groups of insulin are protected with p-methoxy benzoxy carbonylazide (pMZ); Step three, the insulin-pMZ is reacted with the fatty acid ester; Step four, the acylated insulin is deprotected; and Step five, the acylated insulin is isolated and purified. Most notably, selective acylation of one amino group is only achieved by using the pMZ blocking group to protect the other amino groups. Using this methodology, Muranishi and Kiso prepare the following compounds: Lys$^{B29}$-palmitoyl insulin (the ϵ-amino group is acylated), Phe$^{B1}$-palmitoyl insulin (the N terminal α-amino group of the B chain is acylated), and Phe$^{B1}$, Lys$^{B29}$-dipalmitoyl insulin (both the ϵ-amino and the N-terminal α-amino group are acylated).

Similarly, Hashimoto et al., in Pharmaceutical Research 6:171–176 (1989), teach a four step synthesis for preparing N-palmitolyl insulin. The synthesis includes protecting and deprotecting the N-terminal. A$^1$-glycine and the ϵ-amino group of B$^{29}$-lysine, with pMZ. Under the conditions described in the reference, two major acylated products are prepared, B$^1$-mono-palmitoyl insulin and B$^1$, B$^{29}$-dipalmitoyl insulin.

Therefore, prior to the present invention, the selective acylation of the B$^{29}$-N$^{\epsilon}$-amino group of insulin was carried out by protecting and subsequently deprotecting the α-amino groups. The present invention provides a selective one-step synthesis for acylating the ϵ-amino group of proinsulin, insulin and insulin analogs. It is quite surprising that the invention is able to selectively acylate the ϵ-amino group in a one step process in high yield. Thus, the invention eliminates the need to protect and subsequently deprotect other amino groups of the protein. The invention provides more efficient and less expensive means of preparing ϵ-amino acylated insulin derivatives.

SUMMARY OF THE INVENTION

The present invention provides a process of selectively acylating proinsulin, insulin, or an insulin analog having a free ϵ-amino group and a free α-amino group with a fatty acid, which comprises reacting the ϵ-amino group with a soluble activated fatty acid ester under basic conditions in a polar solvent.

DETAILED DESCRIPTION

All amino acid abbreviations used in this disclosure are those accepted by the United States Patent and Trademark Office as set forth in 37 C.F.R. § 1,822(B)(2).

As noted above, the present invention provides a highly selective, one step acylation of the ϵ-amino group of proinsulin, insulin or an insulin analog. The invention specifies conditions that preferentially acylate the ϵ-amino group over the α-amino groups. Generally, the mono-acylated α-amino group is produced in less than 5% yield.

The term "insulin" as used herein means human insulin, pork insulin, or beef insulin. Insulin possesses three free amino groups: B$^1$-Phenylalanine, A$^1$-Glycine, and B$^{29}$-Lysine. The free amino groups at positions A$^1$ and B$^1$ are α-amino groups. The free amino group at position B29 is an ϵ-amino group.

The term "proinsulin" as used herein is a properly cross-linked protein of the formula:

B—C—A wherein:

A is the A chain of insulin or a functional derivative thereof;

B is the B chain of insulin or a functional derivative thereof having an ϵ-amino group; and C is the connecting peptide of proinsulin. Preferably, proinsulin is the A chain of human insulin, the B chain of human insulin, and C is the natural connecting peptide. When proinsulin is the natural sequence, proinsulin possesses two free amino groups: $B^1$-Phenylalanine (α-amino group) and $B^{29}$-Lysine (ϵ-amino group).

The term "insulin analog" as used herein is a properly cross-linked protein of the formula:

A—B wherein:

A is a functional analog of the insulin A chain; and

B is a functional analog of the insulin B chain having an ϵ-amino group.

Preferred insulin analogs include insulin wherein:

the amino acid residue at position $B^{28}$ is Asp, Lys, Leu, Val, or Ala;

the amino acid residue at position $B^{29}$ is Lys or Pro;

the amino acid residue at position $B^{10}$ is His or Asp;

the amino acid residue at position $B^1$ is Phe, Asp, or deleted alone or in combination with a deletion of the residue at position $B^2$;

the amino acid residue at position $B^{30}$ is Thr, Ala, or deleted; and the amino acid residue at position $B^9$ is Ser or Asp; provided that either position $B^{28}$ or $B^{29}$ is Lys.

In standard biochemical terms known to the ordinarily skilled artisan the preferred insulin analogs are $LysB^{28}Pro^{B29}$-human insulin ($B^{28}$ is Lys; $B^{29}$ is Pro); $Asp^{B28}$-human insulin ($B^{28}$ is Asp); $Asp^{B1}$-human insulin, $Arg^{B31},^{B32}$-human insulin, $Asp^{B10}$-human insulin, $Arg^{A0}$-human insulin, $Asp^{B1},Glu^{B13}$-human insulin, $Ala^{B26}$-human insulin, and $Gly^{A21}$-human insulin.

The term "acylating" means the introduction of one or more acyl groups covalently bonded to the free amino groups of the protein.

The term "selective acylation" means the preferential acylation of the ϵ-amino group(s) over the α-amino groups. Generally, selective acylation results in a ratio of the amount of mono-acylated ϵ-amino group product to mono-acylated α-amino group product greater than about 5. Preferably, the ratio is greater than about 10, and most preferably greater than about 50.

The term "fatty acid" means a saturated or unsaturated $C_6$–$C_{21}$ fatty acid. The term "activated fatty acid ester" means a fatty acid which has been activated using general techniques described in Methods of Enzymology 25, 494–499 (1972) and Lapidot et al., in J. of Lipid Res. 8:142–145 (1967). The preferred fatty acids are saturated and include myristic acid ($C_{14}$), pentadecylic acid ($C_{15}$), palmitic acid ($C_{16}$), heptadecylic acid ($C_{17}$) and stearic acid ($C_{18}$). Most preferably, the fatty acid is palmitic acid. Activated fatty acid ester includes derivatives of agents such as hydroxybenzotriazide (HOBT), N-hydroxysuccinimide and derivatives thereof. The preferred activated ester is N-succinimidyl palmitate.

The term "soluble" indicates that a sufficient amount of ester is present in the liquid phase to acylate the insulin, insulin analog or proinsulin. Preferably, about 1 to 4 molar equivalents of activated ester per mole of insulin are in the liquid phase.

The term "basic conditions" as used herein refers to the basicity of the reaction. The reaction must be carried out with all the free amino groups substantially deprotonated. In an aqueous solvent or semi-aqueous solvent mixture, basic conditions means the reaction is carried out at a pH greater than 9.0. In a non-aqueous organic solvent, the reaction is carried out in the presence of a base with basicity equivalent to a $pK_a$ greater than or equal to 10.75 in water.

The term "cross-link" means the formation of disulfide bonds between cysteine residues. A properly cross-linked proinsulin, insulin or insulin analog contains three disulfide bridges. The first disulfide bridge is formed between the cysteine residues at positions 6 and 11 of the A-chain. The second disulfide bridge links the cysteine residues at position 7 of the A-chain to the cysteine at position 7 of the B-chain. The third disulfide bridge links the cysteine at position 20 of the A-chain to the cysteine at position 19 of the B-chain.

Before the present invention, one skilled in the art selectively acylated the ϵ-amino group by the use of a protecting group in a multi-step synthesis. Muranishi and Kiso, Japanese Patent Application 1-254,699, disclose a five-step synthesis for preparing acylated insulin derivatives. Likewise, Hashimoto et al., in Pharmaceutical Research 6:171–176 (1989), teach a four step synthesis for preparing N-palmitoyl insulin. TO selectively acylate the insulin, both references teach the use of the pMZ protecting group.

The present invention produces an $N^{\epsilon}$-acylated proinsulin, insulin, or insulin analog in a high yield, one step synthesis. The reaction permits the preparation of $N^{\epsilon}$-acylated proteins without the use of amino-protecting groups. The acylation is carried out by reacting an activated fatty acid ester with the ϵ-amino group of the protein under basic conditions in a polar solvent. Under weakly basic conditions, all the free amino groups are not deprotonated and significant acylation of the N-terminal amino groups results. In an aqueous solvent or semi-aqueous solvent mixture, basic conditions means the reaction is carried out at a pH greater than 9.0. Because protein degradation results at a pH range exceeding 12.0, the pH of the reaction mixture is preferably pH 9.5 to 11.5, and most preferably 10.5. The pH measurement of the reaction mixture in a mixed organic and aqueous solvent is the pH of the aqueous phase prior to mixing. The data in Table 1 demonstrates the effect of the basicity of the reaction on the selectivity of the reaction. The data presented in Table 1 was generated with human insulin acylated with two molar equivalents N-succinimidyl palmitate in 50% $CH_3CN$/water.

TABLE 1

Effects of pH on the acylation of Insulin

| | Relative amount of product | | |
|---|---|---|---|
| Reaction products | pH 8.2 | pH 9.5 | pH 10.2 |
| Human insulin | 85.2% | 12.5% | 1.6% |
| Mono-acylated A1 and B1 | 8.1% | 0.3% | 0.4% |
| Mono-acylated B29 | 5.2% | 70.2% | 79.6% |
| Bis acylated | 0.7% | 16.7% | 17.7% |
| Ratio of Mono-acylated B29 to Mono-acylated A1 and B1 | 0.64 | 234 | 199 |

Table 1 demonstrates that the acylation of the ϵ-amino group is dependent on the basicity of the reaction. At a pH greater than 9.0, the reaction selectively acylates the ϵ-amino group of B29-lysine.

In a non-aqueous solvent, the reaction is carried out in the presence of a base with basicity equivalent to a $pK_a$ greater than or equal to 10.75 in water in order to sufficiently deprotonate the ε-amino group(s). That is, the base must be at least as strong as triethylamine. Preferably, the base is tetramethylguanidine (TMG), diisopropylethylamine, or tetrabutylammonium hydroxide.

The choice of polar solvent is dependent largely on the solubility of the proinsulin, insulin, or insulin analog and the fatty acid ester. Most significantly, the solvent may be wholly organic. Generally acceptable organic solvents include DMSO, DMF and the like. Aqueous solvent and mixtures of aqueous and organic solvents are also operable. The selection of the polar solvents is limited only by the solubility of the reagents. Preferred solvents and solvent systems are DMSO; DMF; acetonitrile and water; acetone and water; ethanol and water; isopropyl alcohol and water; isopropyl alcohol, ethanol and water; and ethanol, propanol and water. Preferably, the solvent is acetonitrile and water; most preferably 50% acetonitrile. One skilled in the art would recognize that other polar solvents are also operable.

The ratio of the reactants is not critical. Generally it is preferred that the activated fatty acid ester be in molar excess. Preferably the reaction is carried out with 1 to 4 molar equivalents, most preferably 1 to 2 molar equivalents, of the ester. However, one skilled in the art would recognize that at very high levels of activated ester, bis or tri-acylated product will be produced in significant quantity.

The temperature of the reaction is not critical. The reaction is carried out at between 0 to 40 degrees Celsius and is generally complete in 15 minutes to 24 hours.

After acylation, the reaction is quenched, and the product is purified by standard methods such as reverse phase or hydrophobic chromatography. Thereafter, the product is recovered by standard methods such as freeze drying or crystallization.

Proinsulin, insulin and insulin analogs can be prepared by any of a variety of recognized peptide synthesis techniques including classical (solution) methods, solid phase methods, semi-synthetic methods, and more recent recombinant DNA methods. For example, Chance et al., U.S. patent application Ser. No. 07/388,201, EPO publication number 383 472, Brange et al., EPO 214 826, and Belagaje et al., U.S. Pat. No. 5,304,473 disclose the preparation of various proinsulin and insulin analogs and are herein incorporated by reference. The A and B chains of the insulin analogs of the present invention may also be prepared via a proinsulin-like precursor molecule using recombinant DNA techniques. See Frank et al., Peptides: Synthesis-Structure-Function Proc. Seventh Am. Pept. Symp., Eds. D. Rich and E. Gross (1981) which is incorporated herein by reference.

The following examples are provided merely to further illustrate the invention. The scope of the invention is not construed as merely consisting of the following examples.

EXAMPLE 1

Acylation of Insulin Using N-Succinimidyl Palmitate in DMSO

Biosynthetic Human Insulin (BHI) crystals (71.9 mg) were dissolved in 6.58 mL of DMSO. The solution was stirred at room temperature until the crystals were fully dissolved by visual inspection. A solution of activated ester (N-succinimidyl palmitate) was prepared by adding 20 mg of the solid activated ester to 2 mL of DMSO and vigorously stirring until all the activated ester particles were in solution by visual inspection. At that time, 1,1,3,3-Tetramethylguanidine (26.8 μl) was added to 5 mL of the BHI solution, followed by DMSO (94.4 mL) and the previously prepared activated ester solution (400 μl). The reaction was allowed to proceed at room temperature (20° to 25° C.) for approximately 60 minutes. A sample was removed after 15 minutes, diluted 20-fold with 1 N acetic acid and analyzed by HPLC. The reaction yield calculated as the amount of B29-$N^{\epsilon}$-Palmitoyl Human insulin in the quenched sample divided by the initial amount of BHI was 67.1%.

EXAMPLE 2

Acylation of Insulin Using N-Succinimidyl Palmitate in Acetonitrile and Water Biosynthetic Human Insulin (BHI) crystals (199.5 g) were dissolved in 20 L of 50 mM boric acid solution at pH 2.5. The pH of the solution was readjusted to 2.5 using 10% HCl, and the solution was stirred until the crystals were fully dissolved by visual inspection. A sample of the starting material was removed, and the absorbance measured at 276 nm was 10.55. A solution of activated ester (N-Succinimidyl Palmitate) was prepared by adding 24 g of the solid activated ester to 2.4 L of acetonitrile pre-heated to approximately 50° C. and vigorously stirring until all the activated ester particles were in solution by visual inspection. At that time, the pH of the BHI solution was adjusted to approximately 10.22 by the addition of 10% NaOH. Acetonitrile (18 L) was added to the pH adjusted BHI solution. The reaction was allowed to proceed at room temperature (20° to 25° C.) for 110 minutes, then quenched by adding water (123 L) and adjusting the pH of the resulting diluted solution to 2.01 using 10% HCl and 10% NaOH. The reaction yield calculated as the amount of B29-$N^{\epsilon}$-Palmitoyl Human insulin in the quenched reaction divided by the initial amount of BHI was 73%.

EXAMPLE 3

Acylation of $Lys^{B28}Pro^{B29}$-Human Insulin Using N-Succinimidyl Palmitate in Acetonitrile and Water $Lys^{B28}Pro^{B29}$-Human Insulin crystals (2.22 g) were dissolved in 100 mL of 50 mM boric acid solution at pH 2.5. The pH of the solution was readjusted to 2.5 using 10% HCl, and the solution was stirred until the crystals were fully dissolved by visual inspection. A solution of activated ester (N-Succinimidyl Palmitate) was prepared by adding 270 mg of the solid activated ester to 27 mL of acetonitrile pre-heated to approximately 50° C., and vigorously stirring until all the activated ester particles were in solution by visual inspection. The pH of the solution was adjusted to approximately 10.22 by the addition of 10% NaOH, and the solution was allowed to stir at 4° C. for 15 minutes. Acetonitrile (73 mL) was added to the pH adjusted solution, followed by the previously prepared activated ester solution. The reaction was allowed to proceed at 4° C. for 85 minutes, and was quenched by adding 1N acetic acid (600 mL), resulting in a pH of 2.85. The reaction yield calculated as the amount of B28-$N^{\epsilon}$-Palmitoyl $Lys^{B28}Pro^{B29}$-human insulin in the quenched reaction divided by the initial amount of $Lys^{B28}Pro^{B29}$-human insulin was 72.5%.

EXAMPLE 4

Acylation of BHI Using N-Succinimidyl Palmitate in Acetonitrile and Water

Biosynthetic Human Insulin (BHI) crystals (3 g) were dissolved in 300 mL of 50 mM boric acid solution at pH 2.5. The pH of the solution was readjusted as necessary to 2.5 using 10% HCl and the solution was stirred until the crystals were fully dissolved by visual inspection. A solution of activated ester (N-Succinimidyl Palmitate) was prepared by adding 400 mg of the solid activated ester to 40 mL of acetonitrile and vigorously stirring. At that time, the pH of the BHI crystals solution was adjusted to approximately 10.2 by the addition of 10% NaOH. Acetonitrile (240 mL) was then added to the BHI solution followed by the previously prepared activated ester solution. The reaction was allowed to proceed at room temperature (20° to 25° C.) for approximately 90 minutes, then quenched by adding water (1800 mL) and adjusting the pH of the resulting diluted solution to approximately 2.5 using 10% HCl. The reaction yield calculated as the amount of B29-$N^{\epsilon}$-Palmitoyl Human insulin in the reaction divided by the initial amount of BHI was 75.7%.

EXAMPLE 5

Acylation of Proinsulin with N-Succinimidyl Palmitate in Acetonitrile and Water

Human Proinsulin (HPI) aqueous solution (28.2 mg/mL) was diluted with 50 mM boric acid to a final volume of 100 mL at 16.2 mg/mL HPI. The activated ester solution was prepared concurrently by dissolving 150 mg of N-succinimidyl palmitate in 15 mL acetonitrile (ACN) with rapid agitation. The pH of the HPI solution was then adjusted to 10.2 with 10% NaOH followed by the addition of 88 mL ACN. The reaction was initiated by addition of 12 mL activated ester solution (a 2×molar excess over HPI). The final reaction volume was 200 mL, 8 mg/mL HPI in 50% aqueous ACN. The reaction was allowed to proceed at room temperature (20° to 25° C.) for approximately 60 minutes, then quenched by adding an equivalent volume (200 mL) of 50 mM glycine, pH 10.0.

The exact ratios of $\epsilon$-amino acylated species to $\alpha$-amino acylated species were not calculated, the sum of all $\epsilon$-amino acylated species within the chromatogram accounted for 87–90% of the total area, while the sum of all related substances (which would presumably include any $\alpha$-amino acylated species) accounted for <7% of the total area, for any given time point.

EXAMPLE 6

Acylation of $Arg^{B31}$,$Arg^{B32}$ Human Insulin with Hexanoyl-N-Hydroxy-Succinimide Ester $Arg^{B31}$,$Arg^{B32}$ human insulin (1.3 mg) was dissolved in 200 $\mu$L of 200 mM (3-[Cyclohexylamino]-1-propanesulfonic acid) buffer at pH 10.4. Hexanoyl-N-hydroxy-succinimide ester (0.3 $\mu$Moles) dissolved in N,N-Dimethylformamide (DMF) was then added and stirred into solution. The reaction mixture was stirred at ambient temperature (20° to 25° C.) for approximately four hours, then quenched by adjusting the pH to approximately 2.5 using 0.1 N HCl. Gelatinous particles were removed by passing the mixture through a 0.45 micron filter prior to HPLC analysis. Separation of the titled product from starting material was achieved on a $C_4$ reverse phase analytical HPLC column. The reaction yield calculated as the amount of B29-$N^{\epsilon}$hexanoyl-$Arg^{B31}$, $Arg^{B32}$-Human Insulin in the quenched reaction divided by the initial amount of $Arg^{B31}$, $Arg^{B32}$-Human Insulin was 69.4%.

EXAMPLE 7

Acylation of $Leu^{B26}$ Human Insulin with N-Succinimidyl Palmitate in DMSO $Leu^{B36}$-Human Insulin (1.0 mg) was dissolved in 1 mL of 95% Dimethyl Sulfoxide (DMSO), 5% Triethylamine (TEA), N-Succinimidyl palmitate (0.7 $\mu$Moles) dissolved in N,N-Dimethylformamide (DMF) was then added and stirred at ambient temperature (20° to 25° C.) for approximately ninety minutes, then quenched by diluting the sample to 0.2 mg/mL with 0.1N HCl. Gelatinous particles were removed by passing the mixture through a 0.45 micron filter prior to HPLC analysis. Separation of the titled product from starting material was achieved on a $C_4$ reverse phase analytical HPLC column. The reaction yield calculated as the amount of $N^{\epsilon}$-Palmitoyl-$Leu^{B26}$-Human Insulin in the quenched reaction divided by the initial amount of $Leu^{B26}$ Human Insulin was 36.4%.

EXAMPLE 8

Acylation of Human Insulin using N-succinimidyl Palmitate in Dimethylsulfoxide (DMSO)

A solution of insulin was prepared by dissolving Biosynthetic Human Insulin crystals (1 g, 0.17 mmol) completely in 20 mL DMSO at room temperature. At the same time, a solution of activated ester was prepared by dissolving N-succinimidyl palmitate (0.0817 g, 0.23 mmol) in 3 mL DMSO at 50° C. To the insulin solution, which was rigorously stirred, was added first 1,1,3,3-tetramethyguanidine (0.432 mL, 3.4 mmol) and then the entire solution of active ester. After 30 minutes, the reaction was quenched with 120 mL of 0.05 M HCl previously chilled to 0° C. The pH of the mixture was about 1.8. Analysis of the quenched mixture by reverse phase HPLC showed that $B^{29}$-$N^{\epsilon}$-palmitoyl insulin accounted for 72.2% of the total protein eluted, and represented 95% of all mono-acylated insulin.

The entire reaction mixture was loaded on a Vydec C4 preparative reverse phase column (5×25 cm) previously equilibrated with a solvent mixture containing 0.1% trifluoroacetic acid, 20% acetonitrile in water. After loading, the column was first washed with 500 mL of the same solvent, and then developed at a flow rate of 4 mL/minutes and with a solvent system consisting of 0.1% trifluoroacetic acid, acetonitrile and water, wherein the acetonitrile concentration increased from 20 to 80% within 9 L. $B^{29}$-$N^{\epsilon}$-palmitoyl insulin eluted at this solvent system composing of approximately 53% acetonitrile. After removal of the solvent by lyophilization the yield of $N^{\epsilon}$-palmitoyl insulin was 414 mg (0.0684 mmol) or 40.2% based on starting material.

The data in Table 2 demonstrates the selective acylation of insulin, insulin analogs and proinsulin. The experiments were carried out at room temperature with N-hydroxysuccinimide esters of the fatty acid. In the following Table, TMG and TEA represent tetramethylguanidine and triethylamine respectively. ND indicates no data are available.

TABLE 2

| Solvent | Ratio Solvent/ $H_2O$ | Protein | Fatty acid | Base/ pH | % Mono-Acylated (A1 and B1) | % Mono-Acylated ($B^{29}$) | % Bis-Acylated | Ratio monoacyl-B29 to monacyl-A1 and B1 |
|---|---|---|---|---|---|---|---|---|
| DMSO | 100/0 | Insulin | C16 | TMG | <0.1 | 70.7 | 29.3 | >700 |
| DMF | 100/0 | Insulin | C16 | TMG | 0.2 | 71.7 | 15.3 | 359 |
| Acetonitrile | 50/50 | Insulin | C16 | 10.2 | 1.2 | 79.9 | 14.3 | 67 |
| Acetone | 50/50 | Insulin | C16 | 10.2 | 1.1 | 70.8 | 11.8 | 64 |
| Ethanol | 50/50 | Insulin | C16 | 10.2 | 1.6 | 45.6 | 1.9 | 29 |
| IPA | 50/50 | Insulin | C16 | 10.2 | 1.9 | 66.4 | 6.9 | 35 |
| Ethanol/IPA | 50/50 | Insulin | C16 | 10.2 | 1.8 | 50.3 | 2.8 | 28 |
| Ethanol/n-propanol | 50/50 | Insulin | C16 | 10.2 | 2.6 | 49.5 | 2.75 | 19 |
| Acetonitrile | 50/50 | Insulin | C6 | 10.2 | 0.48 | 80.6 | 17.7 | 167 |
| Acetonitrile | 50/50 | Insulin | C8 | 10.2 | 0.37 | 81.4 | 17.1 | 219 |
| Acetonitrile | 50/50 | Insulin | C10 | 10.2 | 0.10 | 83.4 | 14.4 | 834 |
| Acetonitrile | 50/50 | Insulin | C12 | 10.2 | 0.26 | 82.7 | 15.0 | 320 |
| Water | 100 | $Arg^{B31}$, $Arg^{B32}$ - Insulin | C6 | 10.4 | <0.1 | 69.4 | ND | >700 |
| DMF | 60/40 | Insulin | Oleic | 10.4 | 1.1 | 16 | ND | 14 |
| DMF | 60/40 | Insulin | C14 | 10.4 | 3.5 | 47.4 | ND | 14 |
| DMF | 80/10 | Insulin | C18 | TEA | 8.7 | 59.1 | ND | 7 |
| DMF | 80/10 | des (64, 65) proinsulin | C16 | TEA | 5.6 | 31.2 | ND | 6 |
| DMSO | 95/05 | $Leu^{B26}$-Insulin | C16 | TEA | 5.8 | 36.4 | ND | 6.2 |

We claim:

1. A process of selectively acylating proinsulin, insulin, or an insulin analog having one or more free α-amino groups, and a free ε-amino group with a fatty acid, which comprises reacting the ε-amino group with a soluble activated fatty acid ester at pH greater than about 9.0 in a polar solvent.

2. The process of claim 1 wherein the protein is insulin or an insulin analog.

3. The process of claim 2 wherein the protein is human insulin.

4. The process of claim 2 wherein the protein is an insulin analog.

5. The process of claim 4 wherein the protein is $Lys^{B28}Pro^{B29}$-human insulin.

6. The process of claim 1 wherein the activated fatty acid ester is a N-hydroxysuccinimide ester of a $C_{14}$ to $C_{18}$ fatty acid.

7. The process of claim 2 wherein the activated fatty acid ester is a N-hydroxysuccinimide ester of a $C_{14}$ to $C_{18}$ fatty acid.

8. The process of claim 3 wherein the activated fatty acid ester is a N-hydroxysuccinimide ester of a $C_{14}$ to $C_{18}$ fatty acid.

9. The process of claim 4 wherein the activated fatty acid ester is a N-hydroxysuccinimide ester of a $C_{14}$ to $C_{18}$ fatty acid.

10. The process of claim 5 wherein the activated fatty acid ester is a N-hydroxysuccinimide ester of a $C_{14}$ to $C_{18}$ fatty acid.

11. The process of claim 6 wherein the activated fatty acid ester is a N-hydroxysuccinimide ester of palmitic acid.

12. The process of claim 7 wherein the activated fatty acid ester ms a N-hydroxysuccinimide ester of palmitic acid.

13. The process of claim 8 wherein the activated fatty acid ester ms a N-hydroxysuccinimide ester of palmitic acid.

14. The process of claim 9 wherein the activated fatty acid ester is a N-hydroxysuccinimide ester of palmitic acid.

15. The process of claim 10 wherein the activated fatty acid ester ms a N-hydroxysuccinimide ester of palmitic acid.

16. A process of selectively acylating proinsulin, insulin, or an insulin analog having one or more free α-amino groups, and a free ε-amino group with a fatty acid, which comprises reacting the free ε-amino group with a soluble activated fatty acid ester in a semi-aqueous solvent at a pH from about 9.0 to 12.0.

17. The process of claim 16, wherein the protein is human insulin.

18. The process of claim 17, wherein the pH is from about 9.5 to about 10.5.

19. The process of claim 18, wherein the semi-aqueous solvent is acetonitrile and water.

20. The process of claim 19, wherein the solvent is 50% acetonitrile.

21. The process of claim 20, wherein the fatty acid ester is N-succinimidyl palmitate.

*22. A one step process of acylating proinsulin, insulin or an insulin analog having one or more free α-amino groups and a free ε-amino group comprising selectively introducing an acyl group so that it is covalently bonded to the ε-amino group at a pH greater than about 9.0 in an aqueous solvent or a semi-aqueous solvent wherein the ratio of mono-acylated ε-amino insulin, proinsulin or insulin analog to mono-acylated α-amino insulin, proinsulin or insulin analog is greater than about 5.*

*23. The one step process of claim 22 wherein an acyl group is selectively covalently bonded to the ε-amino group of human insulin.*

*24. The one step process of claim 22 wherein an acyl group is selectively covalently bonded to the ε-amino group of an insulin analog.*

*25. The one step process of claim 24 wherein an acyl group is selectively covalently bonded to the ε-amino group of $Lys^{B28}Pro^{B29}$-human insulin.*

*26. The one step process of claim 22 wherein the solvent is a semi-aqueous solvent.*

*27. The one step process of claim 26 wherein the semi-aqueous solvent has a pH of from about 9.0 to 12.0.*

*28. The one step process of claim 27 wherein the semi-aqueous solvent has a pH of from about 9.5 to about 10.5.*

*29. The one step process of claim 28 wherein the semi-aqueous solvent is acetonitrile and water.*

*30. The one step process of claim 29 wherein the semi-aqueous solvent is 50% acetonitrile.*

*31. The one step process of claim 22 wherein the selectively introduced acyl group is a fatty acyl group.*

32. The one step process of claim 22 wherein the ϵ-amino group is reacted with a soluble activated fatty acid ester.

33. The one step process of claim 22 wherein the ratio of mono-acylated ϵ-amino insulin, proinsulin or insulin analog to mono-acylated α-amino insulin, proinsulin or insulin analog is greater than about 10.

34. The one step process of claim 22 wherein the ratio of mono-acylated ϵ-amino insulin, proinsulin or insulin analog to mono-acylated α-amino insulin, proinsulin or insulin analog is greater than about 50.

35. A one step process of acylating proinsulin, insulin or an insulin analog having one or more free α-amino groups and a free ϵ-amino group comprising selectively introducing an acyl group so that it is covalently bonded to the ϵ-amino group in a non-aqueous organic solvent in the presence of a base with a basicity equivalent to a $pK_a$ greater than or equal to 10.75 in water wherein the ratio of mono-acylated ϵ-amino insulin, proinsulin or insulin analog to mono-acylated α-amino insulin, proinsulin or insulin analog is greater than about 5.

36. The one step process of claim 35 wherein an acyl group is selectively covalently bonded to the ϵ-amino group of human insulin.

37. The one step process of claim 35 wherein an acyl group is selectively covalently bonded to the ϵ-amino group of an insulin analog.

38. The one step process of claim 37 wherein an acyl group is selectively covalently bonded to the ϵ-amino group of $Lys^{B28}Pro^{B29}$-human insulin.

39. The one step process of claim 35 wherein the selectively introduced acyl group is a fatty acyl group.

40. The one step process of claim 35 wherein the ϵ-amino group is reacted with a soluble activated fatty acid ester.

41. The one step process of claim 35 wherein the ratio of mono-acylated ϵ-amino insulin, proinsulin or insulin analog to mono-acylated α-amino insulin, proinsulin or insulin analog is greater than about 10.

42. The one step process of claim 35 wherein the ratio of mono-acylated ϵ-amino insulin, proinsulin or insulin analog to mono-acylated α-amino insulin, proinsulin or insulin analog is greater than about 50.

43. A process of acylating proinsulin, insulin or an insulin analog having one or more free α-amino groups and a free ϵ-amino group comprising selectively introducing an acyl group so that it is covalently bonded to the ϵ-amino group without the use of amino-protecting groups at a pH greater than about 9.0 in an aqueous solvent or a semi-aqueous solvent wherein the ratio of mono-acylated ϵ-amino insulin, proinsulin or insulin analog to mono-acylated α-amino insulin, proinsulin or insulin analog is greater than about 5.

44. The process of claim 43 wherein an acyl group is selectively covalently bonded to the ϵ-amino group of human insulin.

45. The process of claim 43 wherein an acyl group is selectively covalently bonded to the ϵ-amino group of an insulin analog.

46. The process of claim 45 wherein an acyl group is selectively covalently bonded to the ϵ-amino group of $Lys^{B28}Pro^{B29}$-human insulin.

47. The process of claim 43 wherein the solvent is a semi-aqueous solvent.

48. The process of claim 47 wherein the semi-aqueous solvent has a pH of from about 9.0 to 12.0.

49. The process of claim 48 wherein the semi-aqueous solvent has a pH of from about 9.5 to about 10.5.

50. The process of claim 49 wherein the semi-aqueous solvent is acetonitrile and water.

51. The process of claim 50 wherein the semi-aqueous solvent is 50% acetonitrile.

52. The process of claim 43 wherein the selectively introduced acyl group is a fatty acyl group.

53. The process of claim 43 wherein the ϵ-amino group is reacted with a soluble activated fatty acid ester.

54. The process of claim 43 wherein the ratio of mono-acylated ϵ-amino insulin, proinsulin or insulin analog to mono-acylated α-amino insulin, proinsulin or insulin analog is greater than about 10.

55. The process of claim 43 wherein the ratio of mono-acylated ϵ-amino insulin, proinsulin or insulin analog to mono-acylated α-amino insulin, proinsulin or insulin analog is greater than about 50.

56. A process of acylating proinsulin, insulin or an insulin analog having one or more free α-amino groups and a free ϵ-amino group comprising selectively introducing an acyl group so that it is covalently bonded to the ϵ-amino group without the use of amino-protecting groups in a non-aqueous organic solvent in the presence of a base with a basicity equivalent to a $pK_a$ greater than or equal to 10.75 in water wherein the ratio of mono-acylated ϵ-amino insulin, proinsulin or insulin analog to mono-acylated α-amino insulin, proinsulin or insulin analog is greater than about 5.

57. The process of claim 56 wherein an acyl group is selectively covalently bonded to the ϵ-amino group of human insulin.

58. The process of claim 56 wherein an acyl group is selectively covalently bonded to the ϵ-amino group of an insulin analog.

59. The process of claim 58 wherein an acyl group is selectively covalently bonded to the ϵ-amino group of $Lys^{B28}Pro^{B29}$-human insulin.

60. The process of claim 56 wherein the selectively introduced acyl group is a fatty acyl group.

61. The process of claim 56 wherein the ϵ-amino group is reacted with a soluble activated fatty acid ester.

62. The one step process of claim 56 wherein the ratio of mono-acylated ϵ-amino insulin, proinsulin or insulin analog to mono-acylated α-amino insulin, proinsulin or insulin analog is greater than about 10.

63. The one step process of claim 56 wherein the ratio of mono-acylated ϵ-amino insulin, proinsulin or insulin analog to mono-acylated α-amino insulin, proinsulin or insulin analog is greater than about 50.

* * * * *